(12) United States Patent
Cleveland (10) Patent No.: US 6,692,701 B2
(45) Date of Patent: Feb. 17, 2004

(54) MICROARRAYER

(75) Inventor: Patrick H. Cleveland, San Diego, CA (US)

(73) Assignee: V & P Scientific, Inc., San Diego, CA (US)

( * ) Notice: Subject to any disclaimer, the term of this patent is extended or adjusted under 35 U.S.C. 154(b) by 0 days.

(21) Appl. No.: 10/315,974

(22) Filed: Dec. 9, 2002

(65) Prior Publication Data

US 2003/0078690 A1 Apr. 24, 2003

Related U.S. Application Data

(62) Division of application No. 09/775,249, filed on Feb. 1, 2001.

(51) Int. Cl.[7] .............................. B01L 9/00; G01N 21/00; G01N 31/00; G01N 33/00; G01N 1/00; B41F 17/00; B41F 45/08
(52) U.S. Cl. ...................... 422/100; 422/103; 422/104; 422/63; 422/99; 436/180; 436/181; 436/174; 101/37; 101/41
(58) Field of Search .......................... 422/99, 100, 103, 422/130, 131, 63; 436/180, 181, 174; 101/37, 41, 60, 93.41; 250/231.13–231.14, 231.15, 231.16, 231.17, 231.18, 231.19; 409/222, 223

(56) References Cited

U.S. PATENT DOCUMENTS

| | | | | | |
|---|---|---|---|---|---|
| 2,012,859 A | * | 8/1935 | Vocke | ............................ | 74/825 |
| 2,369,425 A | * | 2/1945 | Becker | ........................... | 269/85 |
| 2,385,396 A | * | 9/1945 | Baum | ............................ | 33/570 |
| 2,535,490 A | * | 12/1950 | Emrick | ........................... | 477/7 |
| 2,589,554 A | * | 3/1952 | Killian | ....................... | 83/522.25 |
| 2,718,062 A | * | 9/1955 | Cross | ............................ | 33/403 |
| 2,890,606 A | * | 6/1959 | Wahlgren | ................. | 74/813 R |
| 3,541,694 A | * | 11/1970 | Shafer | ........................... | 33/534 |
| 3,638,527 A | * | 2/1972 | Weissenberg | ............... | 409/220 |
| 3,901,658 A | * | 8/1975 | Burtis et al. | ................. | 422/104 |
| 3,965,936 A | * | 6/1976 | Lyon | ..................... | 137/625.17 |
| 4,507,977 A | * | 4/1985 | Cabrera | .................... | 73/864.12 |
| 4,690,801 A | * | 9/1987 | Anderson | ..................... | 422/61 |
| 4,702,889 A | * | 10/1987 | Cabrera et al. | ............. | 422/103 |
| 4,726,932 A | * | 2/1988 | Feier et al. | .................. | 422/103 |
| 4,847,205 A | * | 7/1989 | Burtis et al. | ................... | 436/45 |
| 4,948,565 A | * | 8/1990 | Bemis et al. | ................ | 422/103 |
| 4,963,732 A | * | 10/1990 | Saito | ...................... | 250/231.13 |
| 5,057,684 A | * | 10/1991 | Service | ................... | 250/231.13 |
| 5,061,381 A | * | 10/1991 | Burd | ........................... | 210/789 |
| 5,122,284 A | * | 6/1992 | Braynin et al. | ............. | 210/782 |
| 5,558,839 A | * | 9/1996 | Matte et al. | ................. | 422/101 |
| 5,708,496 A | * | 1/1998 | Barnett et al. | ................. | 356/28 |
| 5,734,160 A | * | 3/1998 | Chung et al. | .......... | 250/231.13 |
| 6,328,508 B1 | * | 12/2001 | Jines | ........................... | 409/221 |
| 6,555,808 B2 | * | 4/2003 | Takeuchi et al. | ....... | 250/231.13 |

* cited by examiner

Primary Examiner—Jill Warden
Assistant Examiner—Brian R Gordon
(74) Attorney, Agent, or Firm—McDermott, Will & Emery (57) ABSTRACT

A device for providing incremental translation in multiple directions, having a base plate (3), a first plate (1), a second plate (2) and means for translation, such as differentially spaced holes (4,5). When the device includes an optional separate applicator (8) with pins (6) for delivering a specimen to a surface (3d), such as a slide, the device can be used in a method for making microarrays.

27 Claims, 6 Drawing Sheets

MICROARRAYER

This application is a divisional of application Ser. No. 09/775,249, filed Feb. 1, 2001.

BACKGROUND OF THE INVENTION

The present invention relates to the field of mechanical devices and more particularly to devices that provide incremental translation.

Recent advances in biotechnology have made a seemingly limitless number of new substances available for study. Combinatorial chemistry has generated millions of compounds, some of which may prove to be life-saving drugs. The Human Genome Project and the Human Proteome Project both promise to yield hundreds of thousands of previously unknown sequences and proteins that may lead to the development of new therapies for diseases. But the availability of these substances is not enough: they must be screened for usefulness. Their overwhelming number makes screening a daunting task.

One solution is to transfer small samples of the substances onto a surface, such a microscope slide. Over ten thousand substances can be fixed on a single slide by making discrete spots of the samples in a dense grid-like pattern. The result is a "microarray" where all the spots can be tested simultaneously for usefulness while on the slide. If a particular spot looks promising, the substance can be identified by its position on the slide and tested further.

Machines for making microarrays can be enormously expensive, limiting their availability to researchers. The machines can also require complex automation to spot the slides accurately and at such high densities. Accordingly, there is a need for a device that can make microarrays, but is not prohibitively expensive and does not require extensive automation. This invention satisfies these needs and provides related advantages as well.

SUMMARY OF THE INVENTION

The present invention provides a device that can provide translation in multiple directions in fixed increments. The device has a base plate, a first plate and a second plate. The first plate is slidable relative to the base plate in a first direction, and the second plate is slidable relative to the first plate in a second direction. The device also has means for translating the plates in individual increments.

An example of a translating means is a first set of holes in one of the plates and a second set of holes in another of the plates. When measured in the direction of translation, the centers of the first set of holes are spaced apart by a first spacing, and the centers of the second set of holes are spaced apart by a second spacing. The spacing of the holes is predetermined so that the difference between the first spacing and the second spacing, when measured in the direction of translation, is equal to the individual increment. Incremental translation can then be achieved by inserting an optional pin or other implement into the holes sequentially.

When the device includes a separate applicator with pins that can deliver a specimen to a surface, such as a slide, the device can be used to make microarrays. The method involves placing a specimen-receiving surface in the device; applying various solutions to specimen-delivering pins of the applicator; and transferring samples of the solutions to the specimen-receiving surface. The transfer can be repeated several times in one direction, translating each time by an increment, to create a row. Several rows each are then repeated incrementally in a second direction to create a column and subsequently obtain a microarray.

Throughout the figures and the rest of the specification, the following numbers are used:

| | | |
|---|---|---|
| 1 | first plate | |
| | 1a | window |
| | 1b | groove for accepting peg 2c |
| | 1c | groove for accepting peg 3b |
| | 1d | first direction of translation |
| 2 | second plate | |
| | 2a | window |
| | 2b | peg for aligning slot 8b |
| | 2c | peg for sliding in groove 1b |
| | 2d | second direction of translation |
| | 2e | attachment bolt |
| 3 | base plate | |
| | 3a | bay |
| | 3b | peg for sliding in grove 1c |
| | 3c | tension arm |
| | 3d | specimen-receiving surface |
| 4 | first set of holes for direction 1d | |
| | 4a, 4b, 4c | individual holes |
| | 4d | diameter of a hole |
| | 4e | first spacing in the direction of translation |
| | 4g | interior wall |
| 5 | second set of holes for direction 1d | |
| | 5a, 5b, 5c | individual holes |
| | 5d | diameter of a hole |
| | 5e | second spacing in the direction of translation |
| | 5f | individual increment in the direction of translation |
| | 5g | upper rim |
| 6 | pin | |
| | 6a | pin tip |
| 7 | direction of cross-sectional view in FIG. 7 | |
| 8 | applicator | |
| | 8a | specimen-delivery pins |
| | 8b | slot |
| | 8c | depressible bumper |
| | 8d | rubber cushion |
| 9 | first set of holes for direction 2d | |
| 10 | second set of holes for direction 2d | |

DETAILED DESCRIPTION OF THE INVENTION

The present invention provides a device for incremental translation in at least two directions. In combination with a separate specimen-applicator, the device allows the applicator to be used repeatedly, translating between individual uses so that the applicator applies a specimen to a different position each time. A particularly useful application for the device is for making dense patterns of individual substances on a surface, such as a slide, which can then be used as a microarray.

Figure 1:
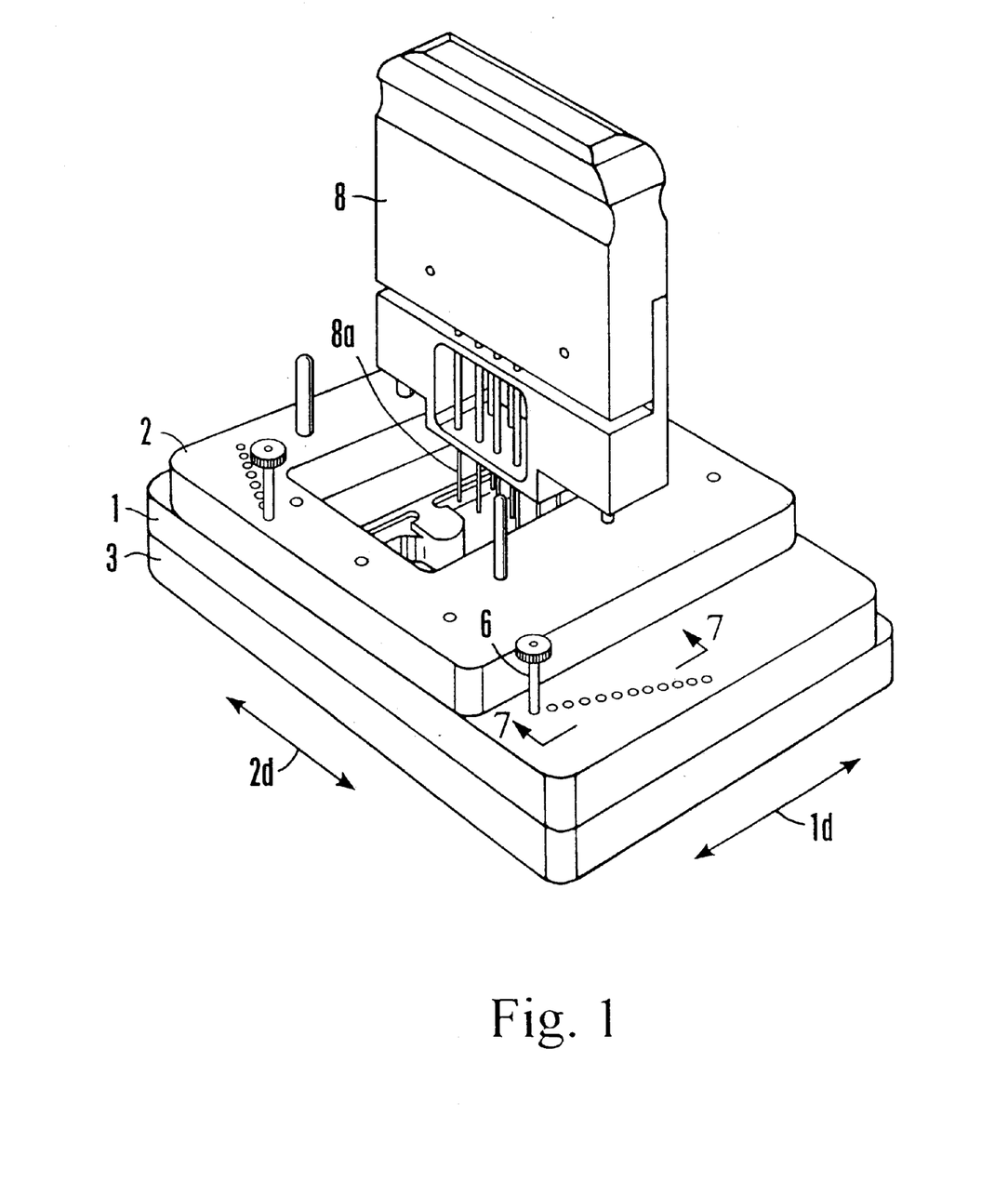
FIG. 1 shows a three-quarter view of one embodiment of the device.

Although the full range of devices encompassed within the invention is limited only by the claims, the embodiment in FIG. 1 is used here as an example to illustrate the features of the device. The device has a base plate 3, a first plate 1 and a second plate 2. These plates are shown in more detail from above and below in the exploded view in FIG. 2.

Figure 2:
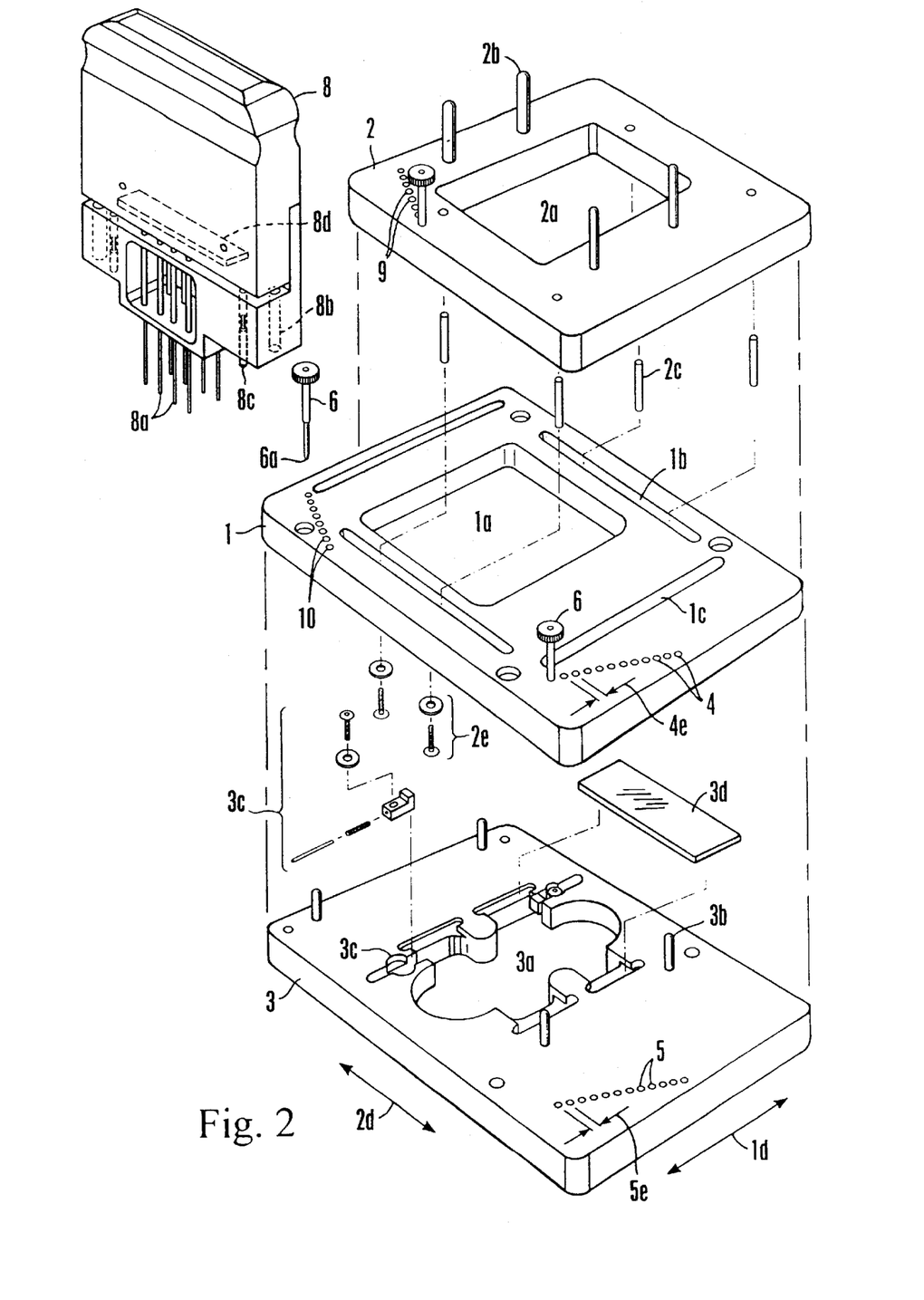
FIG. 2 shows an exploded view of the device from above.

The first plate 1 can slide relative to the base plate 3 in a first direction 1d. Similarly, the second plate 2 is slidable relative to the first plate 1 in a second direction 2d. Although the first and second directions can be any two directions, they are orthogonal in this illustration. Moreover, the total range of the sliding movement need only be for a certain distance to be useful, for example less than 5, 4, 3 or 2 centimeters.

When a particular plate can move or slide in a particular direction, it may be convenient to limit undesirable movement in other directions as long as it does not substantially affect the freedom of the plate to move in the desired direction.

For the example, the first plate 1 should be able to move in the first direction 1d relative to the base plate 3, but it may be desirable to restrict its movement in the second direction 2d. To do this, the base plate can have one or more pegs 3b that fit into corresponding grooves 1c in the first plate. When the pegs can slide in the grooves in the first direction, the first plate can move in the first direction, but not substantially in the second direction.

Similarly, the second plate 2 can also be restricted in the first direction 1 when the second plate has one or more pegs 2c, and the first plate has corresponding grooves 1c oriented lengthwise in the second direction 2d and the pegs are slidably inserted in the grooves.

Other means for restricting undesired movement include using a single peg and a single groove, or using one or more grooves with a capture rail on at least one outside edge to prevent the a from becoming disengaged from the groove. Yet another restricting means is to mount the two plates to a linear bearing.

In certain embodiments, it may be useful for the plates to be freely detachable from each other. In others, the first plate may be non-detachable from the base plate and/or the second plate may be non-detachable from the first plate, depending on the particular application for the device. For example in FIG. 2, the first plate and base plate are attached by a means for attaching, such as an attachment bolt 2e, screw, clamp or adhesive.

The device also has means for translating the plates relative to each other: a first means for translating the first plate in the first direction and a second means for translating the second plate in the second direction. Each translation means can move two plates relative to each other by a number of individual increments in a particular direction.

The individual increment can be as small as 0.1, 0.2, 0.4, 0.5, 0.75, 1 or 2 millimeters. The increment can also be as large as 10, 9, 7, 5, 4.5, 2, 1.5, 1 or 0.5 millimeters. The total number of increments in any direction can be at least 2, 4, 5, 8, 9, 10, 12, 16, or 20 increments, or at most 100, 96, 50, 48, 40, 30, 24, 20, 12 or 9 increments. While it is generally desirable for the increments in a given direction to be equal to each other, various embodiments having unequal increments are encompassed within the invention.

A particular means for translating two plates relative to each other involves a first set of holes in the first plate and a second set of holes in the second plate. The holes should pass completely through one plate, but need not pass completely through the second plate. In FIG. 2, for example, the holes in base plate 3 pass completely through, while the holes in FIG. 7a do not. Although the holes can be arranged in virtually any configuration, their operation is most easily explained when they are arranged in a line.

Figure 7A:
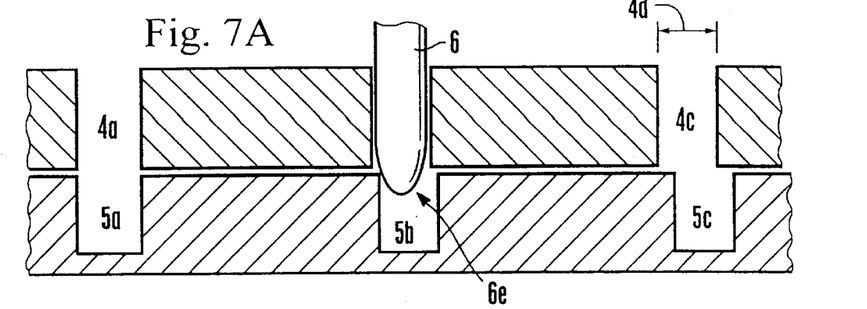
FIGS. 7a to 7d illustrate a mechanism for translating the plates.

In FIG. 2, for example, the means for translating the first plate 1 relative to the base plate 3 includes a set of holes 5 arranged in a line in the base plate 3 and a corresponding set of holes 4 in the first plate 1. A cross-sectional view is shown in FIG. 7a, where the direction of the view is marked 7 in FIG. 1. Similarly, a second means can be provided for translating the second plate 2 relative to the first plate 1, such as a set of holes 9 in the second plate 2 and a set of holes 10 in the first plate 1. For convenience of discussion, useful mechanisms for the set of holes will be described generically for a first set of holes and a second set of holes, regardless of whether they are on the first, second or base plates.

In this embodiment, the individual centers of the first set of holes are spaced apart by a first spacing 4e when measured in the direction of translation 1d. It should be noted that this direction 1d is not necessarily the same direction as the linear arrangement of the holes themselves, but only appears so in cross-section. The centers of the second set of holes are also spaced apart by a second spacing 5e in the direction of translation 1d. The first and second spacings are predetermined so that the difference between the first spacing and the second spacing is equal to the individual increment 5f in the direction of translation.

It is particularly useful when the diameter of the holes 4d, 5d is greater than twice, 2.5, 3, 4 or even 5 times the individual increment, as is the case in FIG. 7a. As shown, the first plate 1 and the base plate 3 are positioned so that one hole 4a in the second plate is vertically aligned with the corresponding hole 5a in the first plate.

At this point, a pin 6 may be inserted freely into holes 4a and 5a. Any instrument can be used as a pin as long as it can be inserted simultaneously through a hole of the first set of holes and partially into or completely through a hole of the second set of holes. The pin can have a cross-sectional shape that is substantially the same as the cross-sectional shape of the holes of the first and second sets, whether round, polygonal, or some other shape.

Once the plates are positioned as shown in FIG. 7a, the pin 6 can be inserted into adjacent hole 4b. A pin having a convex tip 6a can facilitate its insertion into the hole 5b of the second set. The convex tip can be substantially hemispherical, conical, paraboloid, pyramidal or a frustum.

Figure 7B:
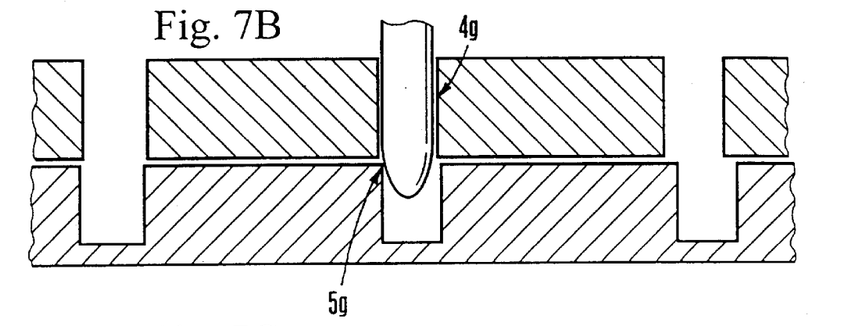
Figure 7C:
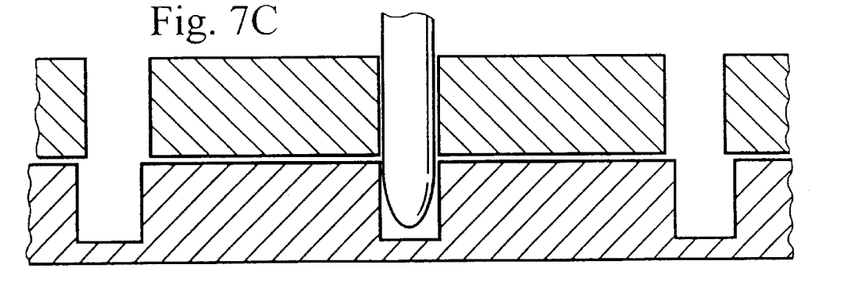
Figure 7D:
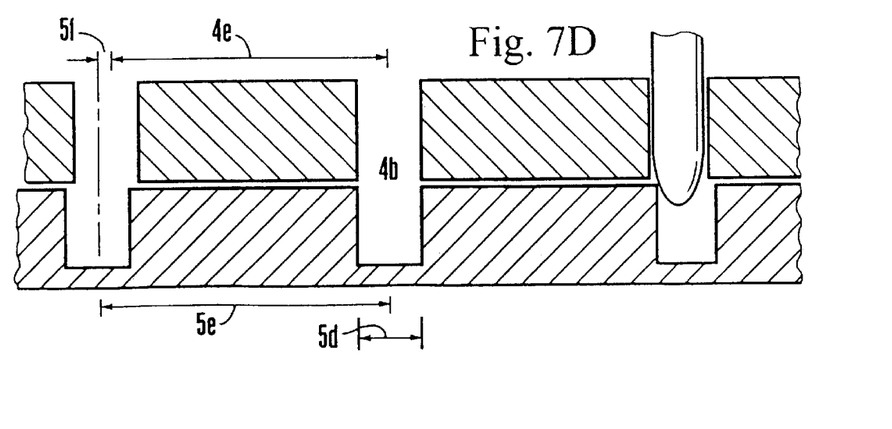

Due to the relative positions of the plates, the pin may not enter corresponding hole 5b freely, as shown in FIG. 7b, but can contact the upper rim 5g of hole 5b. As shown in FIG. 7b, applying downward pressure to the pin will force the pin to wedge the upper rim 5g of hole 5b away from the opposite interior wall 4g of hole 4b, effectively pushing the second plate 2 to the right. As shown in FIG. 7c, the completed shifting action results in a translation of the incremental distance 5f in the second direction 2d.

Once this translation is complete, the plates are aligned so that the pin can be removed from holes 4b and 5b and inserted into adjacent hole 4c so that the shifting can be repeated in hole 5c, resulting in a second incremental translation in the second direction. The translation can then be repeated for as many holes are in the two sets.

To summarize, a plate of the device can be translated by starting where a hole in a first set of holes is aligned with a hole in a second set of holes. Then, a pin is inserted through a different hole in the first set and into a different hole in the second set. As a result, the plate is translated in one direction by an increment. It should be noted that this and the other methods disclosed herein can be performed equally well manually or using automation.

Use of the device does not require the diameter of the holes to be greater than twice the individual increment. The translation steps can be achieved by hand or machine by shifting one of the plates and using the pin to confirm that the plates have been translated by the desired incremental distance. For example, starting with FIG. 7c, the pin can be removed from holes 4b and 5b and inserted into hole 4c. Then the second plate 2 is shifted to the right until the pin is allowed to fall into hole 5c. Alternatively, slight downward pressure can be applied to the pin while sliding the second plate to ensure that the pin slides into hole 5c, thereby insuring that the first plate has been translated by the incremental distance.

Given the mechanisms described above, the simplest arrangement of the holes is linearly in the direction of translation. However, the holes can also be arranged linearly in a direction oblique to the direction of translation, so long as the incremental spacing in the direction of translation is maintained between the holes Stated differently, if the direction of translation defines a plane, and the positions of the holes are projected onto the plane, then the distance between the centers of the holes should be the incremental distance when measured on the surface of the plane.

Figure 6A:
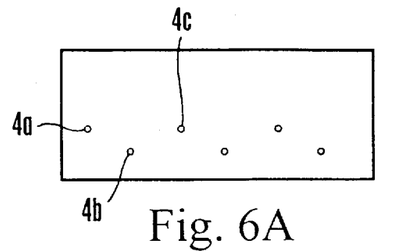
FIGS. 6a to 6d show examples of nonlinear arrangements for the holes.
Figure 6B:
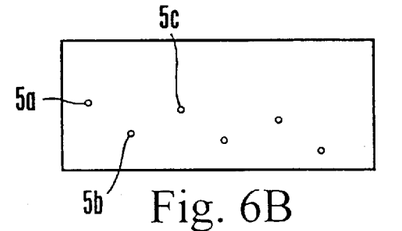
Figure 6C:
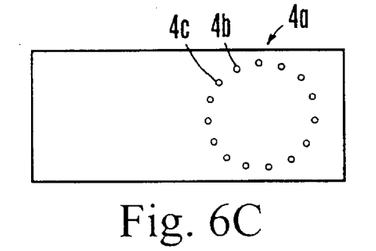
Figure 6D:
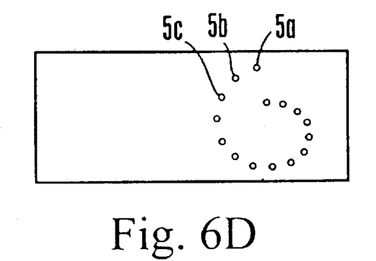

In fact, the holes need not be arranged in a line at all, but may be arranged in a substantially linear arrangement, in a staggered sequence or in a circle, so long as the incremental spacing is maintained between different holes, whether adjacent or not. For example, FIG. 6a shows a staggered arrangement of holes that can be used in one plate with the arrangement in FIG. 6b in another plate, so that nonlinear or nonadjacent holes are used sequentially, starting with holes 4a/5a, 4b/5b and 4c/5c. Similarly, the circular arrangement in FIG. 6c can be used with the arrangement in FIG. 6d, starting with holes 4a/5a, 4b/5b and 4c/5c, to achieve translation in direction 1d.

Other means for translating the plates need not be limited to the use of differentially spaced holes. For example, one plate can have a detent that engages a series of notches in the other plate, where the notches are spaced apart by the incremental distance. One or both plates can have a toothed strip that engages a gear that can be turned by a predetermined rotation, thereby translating the plates relative to each other by the incremental distance. Other means include a ratchet, a threaded screw, or a perforated or ribbed strip, each of which allows plates to be translated in multiple increments.

Additional means for translation can be used in a particular direction. In certain cases, it may be desirable to translate in small increments in a first region, and then translate in small increments in a second region that is relatively distant to the first region. Thus, the device can have a means for translating a plate by a second increment, where the second increment is greater than the total distance of the individual increments in preselected a direction.

Thus far, the device has been described in terms of its ability to provide translation. The device can also be used to hold a specimen-receiving surface 3d, such as a slide by having a means for holding the specimen-receiving surface. The holding means should securely position the surface substantially between the base plate and the first plate, or within the base plate, as long as it is substantially immobilized relative to the base plate. A particular holding means is a bay 3a in the base plate. The means can further have one or more tension arms 3c for securing the specimen-receiving surface in the bay. The tension arm can be any solid that can apply pressure to the specimen-receiving surface to substantially immobilize the surface relative to the base plate. An example of a tension arm is a spring attached at one end to the base plate, where the other end contacts a slide via a plastic pad. Other examples include a clamp, adjustable belt or elastic band, brace, removable screw or pin, spring clip, a frame that covers a portion of the perimeter of the surface, or a semi-adhesive surface.

The device can also include a separate applicator 8 having one or more specimen-delivering pins 8a. The unit can be attachable to the second plate so that the pins point toward a specimen-receiving surface 3d when the surface is secured by the holding means. To provide the pins with access to the specimen-receiving surface, the first and second plates can have windows 1a, 2a.

To facilitate the secure attachment of the applicator to the second plate, the second plate can have one or more alignment pegs 2b, and the applicator can have at least one slot 8b so that each peg can be inserted in a corresponding slot. If more than one peg is used, they can be of different sizes or shapes to ensure that the applicator is attached in the correct orientation.

The pins should be capable of transferring a substance, either in solid or liquid form, to the specimen-receiving surface. For stability, it can be useful for the pins to be relatively fixed or resistant to translating in the first and second directions. Nevertheless, the pins can be relatively free in their lengthwise direction, as long as they are capable of contacting the specimen-receiving surface.

In a particular embodiment, the applicator can have a depressible bumper 8c to prevent contact between the applicator and the second plate 2. Thus, the bumper can be sized so that when the applicator rests on the second plate 2, the specimen-delivering pins do not contact the specimen-receiving surface. But when the bumper is depressed, the specimen-delivering pins of the applicator do contact the specimen-receiving surface. Upon contact, the pins can "float" up into an optional rubber cushion 8d to prevent the pins from being damaged by the contact.

Figure 5A:
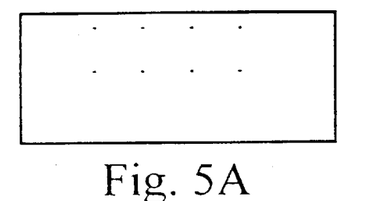
FIGS. 5a to 5e illustrate a sequence of spotting steps to make a microarray.

With the applicator, the device can be used in a method for transferring solutions or other substances to a specimen-receiving surface. The method involves placing a specimen-receiving surface in the holding means and applying one or more solutions to the specimen-delivering pins of the applicator. Next, the applicator is attached to the second plate. The solution on the specimen-delivering pins is then transferred to the specimen-receiving surface. Where the applicator has a 2×4 pattern of 8 specimen-transferring pins, this first transfer is represented in FIG. 5a.

Figure 5B:
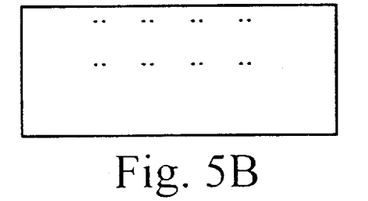
Figure 5C:
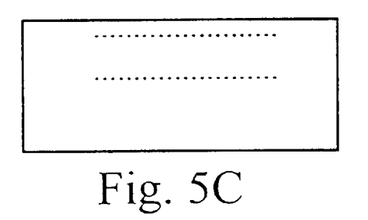

After the first transfer, the plates are translated in the first direction by one increment, and the transfer is repeated as described above, yielding the spotting pattern shown in FIG. 5b. The spotting and translation can then be repeated for the number of increments in the first direction to make a complete row, as shown in FIG. 5c.

Figure 5D:
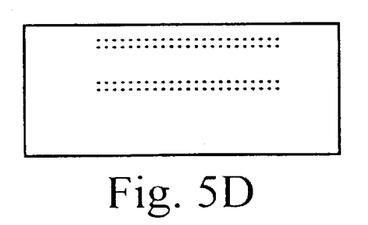
Figure 5E:
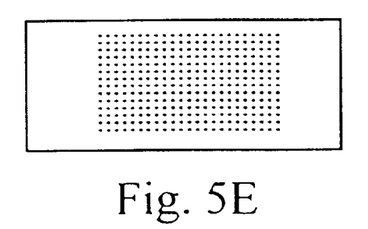

Once the first row is completed, the second plate is translated by one increment in the second direction. Another row of spots is generated by repeating the steps above, shown in FIG. 5d. Several rows can be spotted in this way, yielding a pattern as in FIG. 5e.

To optimize the spacing of the pattern, the spots made by the pins can be spaced in the first direction by a distance greater than or equal to the number of increments in the first direction multiplied by the increment distance in the first direction. Similarly, the spots can be spaced in the second direction by a distance greater than or equal to the number of increments in the second direction multiplied by the increment distance in the second direction.

The result of repeating the transfer and translation steps in both the first and second directions is a densely ordered pattern of spotted substances on the surface, which can then be used as a microarray.

Figure 3:
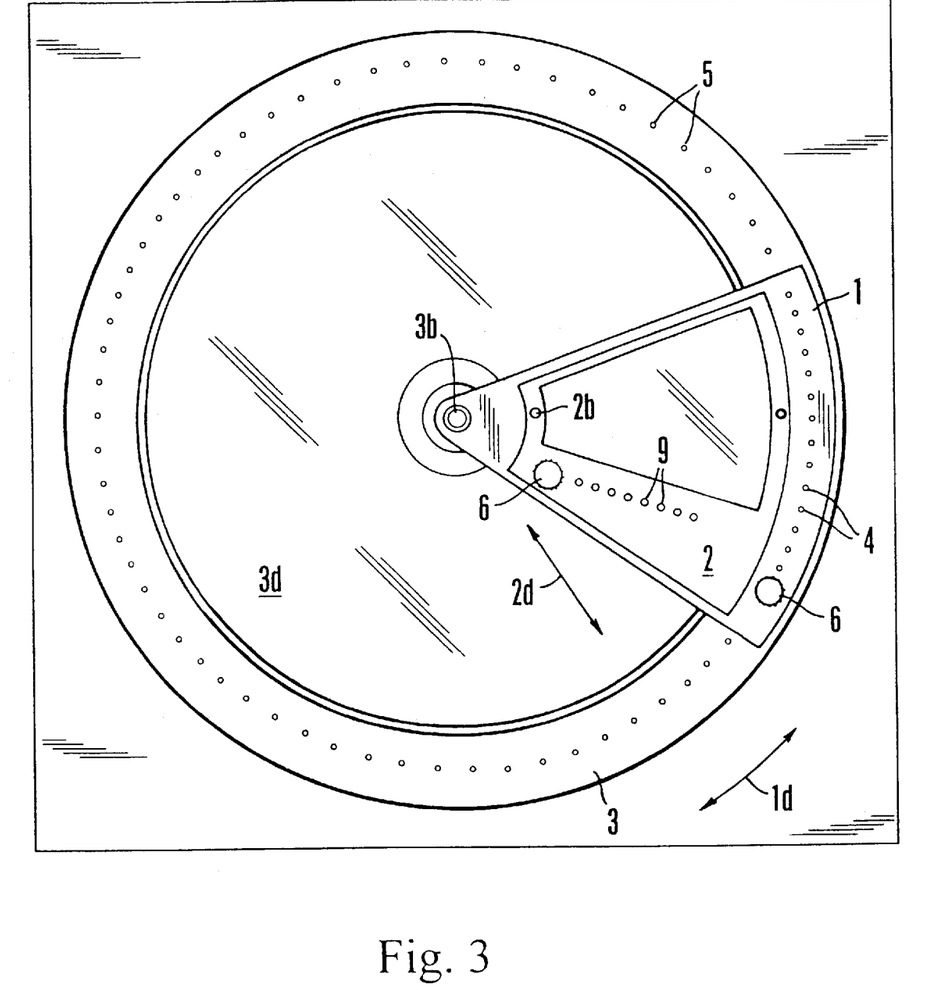
FIG. 3 shows a top view of a radial embodiment of the device.
Figure 4:
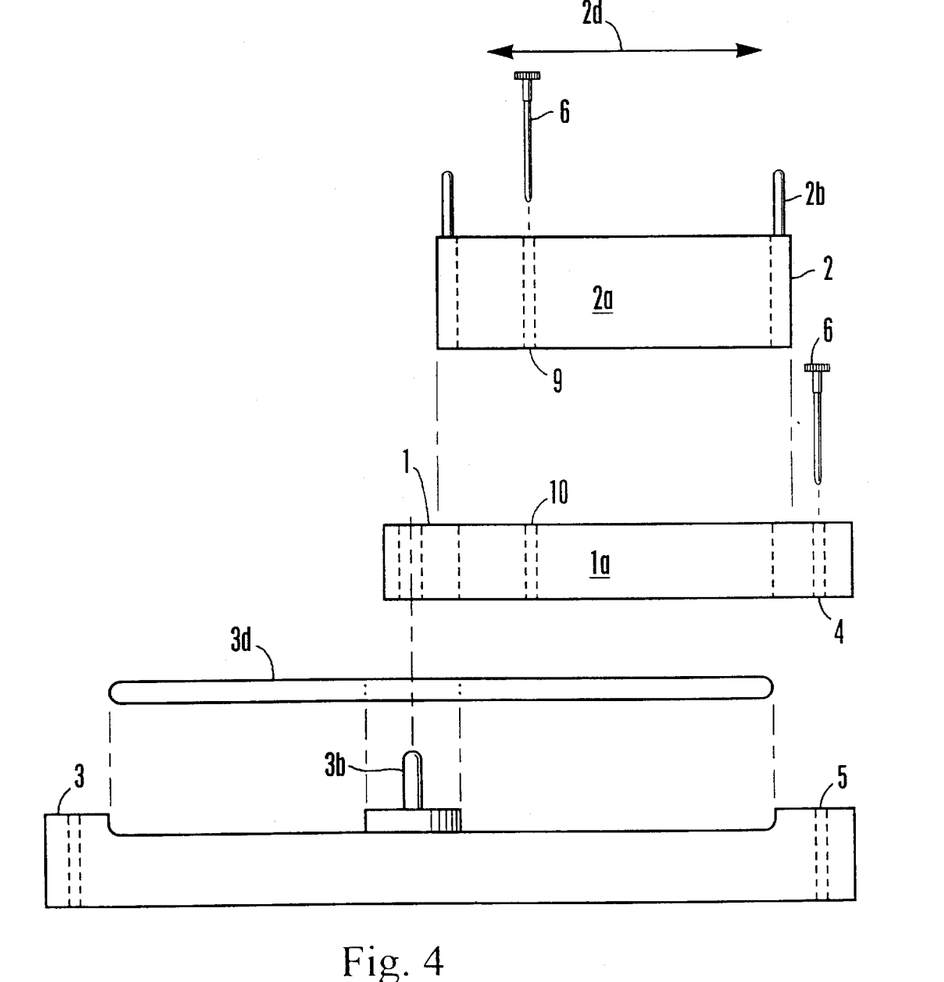
FIG. 4 shows a side view of the radial embodiment of the device.

The device of the invention is not limited to rectangular grids, but can be extended to devices for making radial microarrays, such as on a compact disc or other nonrectangular shape. As shown in FIGS. 3 and 4, a radial device works on essentially the same principles as discussed above and is included within the present invention.

Thus, the present invention also provides a device having a base plate 3 that can optionally hold a specimen-receiving surface 3d; a first plate 1 that is rotatably fixed to the base plate 3 at one point, such as a peg 3b; and a second plate 2 that is slidable relative to the first plate 1 in a rotation direction 1d. The radial device also has a first means for rotating the first plate in individual increments, such as a set of holes 4 in the first plate 1 and a second set of holes 5 running along a portion of the perimeter of the base plate 3. The total number of increments in the rotation direction can be at least 20, 50, 100, or 200 increments, or at most 10,000, 5000, 2000, 1000, 500, 200 or 100 increments.

A second means for translating is then provided so that the second plate can move in a radial direction 2d in individual increments, such as a set of holes 9 in the second plate 2 and a second set of holes 10 in the first plate 1. The total number of increments in the rotation direction can be at least 2, 4, 5, 8, 9, 10, 12, 16 or 20 increments, or at most 100, 96, 50, 48, 40, 30, 24, 20, 12, 9 or 8 increments. The radial device can then have a corresponding applicator that can be attached to the second plate 2, with pins that can contact the specimen-receiving surface 3d. The pins can be arranged in a sector or pie-slice-shaped format to optimize the pattern of spots when the radial device is used to make microarrays. The other features of the radial device shown in FIGS. 3 and 4 are essentially as described above.

Although the invention has been described with reference to the disclosed embodiments, those skilled in the art will readily appreciate that the specific examples detailed are only illustrative of the invention. It should be understood that various modifications can be made without departing from the spirit of the invention. Accordingly, the invention is limited only by the following claims.

I claim:

1. A device, comprising
   a base plate;
   a first plate, wherein one part of the first plate is rotatably fixed to the base plate and the other part of the first plate is slidable relative to the base plate in rotation;
   a second plate, wherein the second plate is slidable relative to the first plate in an radial direction;
   first means for moving the first plate in rotation in individual increments and for a total of at least two possible increments;
   second means for moving the second plate in the radial direction in individual increments and for a total of at least two possible increments;
   wherein at least one of the means for moving comprises
   a first set of holes in one of the plates and
   a second set of holes in another of the plates;
   wherein the centers of the first set of holes are spaced apart by a first spacing when measured in the direction of movement;
   wherein the centers of the second set of holes spaced apart by a second spacing when measured in the direction of movement; and
   wherein the difference between the first spacing and the second spacing is the individual increment in the direction of movement.

2. The device of claim 1, wherein the diameter of the holes is at most twice the individual increment.

3. The device of claim 1, wherein the diameter of the holes is greater than twice the individual increment.

4. The device of claim 1, wherein the diameter of the holes is at least 3 times greater than twice the individual increment.

5. The device of claim 1, wherein the diameter of the holes is at least 5 times greater than twice the individual increment.

6. The device of claim 1, further comprising a pin, wherein the pin can be simultaneously inserted through a hole of the first set and into a hole of the second set.

7. The device of claim 6, wherein the tip of the pin is convex.

8. The device of claim 6, wherein the cross-sections of the pin and the holes of the first and second sets are substantially the same shape.

9. The device of claim 8, wherein the cross-sections of the holes and the pin are round.

10. The device of claim 8, wherein the cross-sections of the holes and the pin are polygonal.

11. A method for moving a plate, comprising the steps of
    (a) obtaining the device of claim 6, wherein a hole in a first set of holes is aligned with a hole in a second set of holes;
    (b) inserting a pin through a different hole in the first set and into a different hole in the second set;
    whereby the plate is moved in one direction by an increment.

12. A method for moving a plate in one direction by a predetermined increment, comprising the steps of
    (a) obtaining the device of claim 6, wherein a hole in the first set is aligned with a hole in the second set;
    (b) moving the plate in one direction;
    (b) allowing a pin inserted into a different hole in the first set to be inserted into a different hole in the second set;
    whereby the plate is moving in one direction by a predetermined increment.

13. A method for making a microarray, comprising the steps of
    (a) placing a specimen-receiving surface in the holding means of the device of claim 6;
    (b) applying at least one solution to the specimen-delivering pins of the applicator; and
    (c) attaching the applicator to the second plate,
    whereby solution on the specimen-delivering pins is transferred to the specimen-receiving surface.

14. The method of claim 13,
    wherein steps (b) and (c) are repeated for a plurality of increments in one direction;
    wherein one plate is moved by one increment after each repetition.

15. The method of claim 14,
    wherein steps (b) and (c) are repeated for a plurality of increments in another direction; and
    wherein another plate is moved by one increment after each repetition.

16. A device, comprising
    a base plate;
    a first plate, wherein one part of the first plate is rotatable fixed to the base plate and the other part of the first plate is slidable relative to the base plate in rotation;
    a second plate, wherein the second plate is slidable relative to the first plate in an radial direction;
    first means for moving the first plate in rotation in individual increments and for a total of at least two possible increments;
    second means for moving the second plate in the radial direction in individual increments and for a total of at least two possible increments;
    wherein at least one of the means for moving comprises an indexing notch and an element selected from the group consisting of a clip, spring detent and ball detent.

17. A device, comprising a base plate;

a first plate, wherein one part of the first plate is rotatably fixed to the base plate and the other part of the first plate is slidable relative to the base plate in rotation;

a second plate, wherein the second plate is slidable relative to the first plate in an radial direction;

first means for moving the first plate in rotation in individual increments and for a total of at least two possible increments;

second means for moving the second plate in the radial direction in individual increments and for a total of at least two possible increments;

wherein the base plate further has at least one means for holding a specimen-receiving surface substantially between the base plate and the first plate or in the base plate; and wherein the first plate and the second plate each has a window permitting access to the holding means.

18. The device of claim 17, wherein the holding means is in the base plate.

19. The device of claim 18, wherein the holding means comprises a bay in the base plate.

20. The device of claim 19, wherein the holding means further comprises a tension arm for securing the specimen-receiving surface in the bay.

21. The device of claim 17, wherein the device has at least two holding means.

22. The device of claim 17, further comprising a separate applicator that can be removably attached to the second plate, wherein the applicator comprises a plurality of specimen-delivering pins that point toward the holding means when attached to the second plate.

23. The device of claim 22, wherein the specimen-delivering pins are spaced in a first direction by a distance greater than or equal to the number of increments in the first direction multiplied by the increment distance in the first direction.

24. The device of claim 22, wherein the specimen-delivering pins are spaced in a second direction by a distance greater than or equal to the number of increments in the second direction multiplied by the increment distance in the second direction.

25. The device of claim 22, wherein the second plate comprises at least one peg, and the applicator has at least one slot, wherein each peg can be inserted in a corresponding slot.

26. The device of claim 22, wherein the applicator further comprises a depressible bumper, whereby when the applicator is attached to the second plate and the base plate contains a specimen-receiving surface, the specimen-delivering pins of the applicator do not contact the specimen-receiving surface, but when the bumper is depressed, the specimen-delivering pins of the applicator contact the specimen-receiving surface.

27. The device of claim 22, wherein the specimen-delivering pins are fixed in the first and second directions, but are not fixed in the lengthwise direction of the specimen-delivering pins.

* * * * *